United States Patent [19]

Sperling

[11] 4,035,079
[45] July 12, 1977

[54] METHOD OF AND DEVICE FOR INVESTIGATING SAMPLES BY A FLAME-FREE ATOM ABSORPTION PROCESS

[75] Inventor: Klaus-Richard Sperling, Hamburg, Germany

[73] Assignee: The Federal Republic of Germany represented by Bundesministerium fur Forschung und Technologie, Bonn, Germany

[21] Appl. No.: 609,218

[22] Filed: Sept. 2, 1975

[30] Foreign Application Priority Data

Apr. 18, 1975 Germany .......................... 2517163

[51] Int. Cl.² ..................... G01J 3/30; G01N 21/16
[52] U.S. Cl. ................................... 356/85; 356/244
[58] Field of Search ............................. 356/85, 244

[56] References Cited

U.S. PATENT DOCUMENTS

| 3,702,219 | 11/1972 | Braun et al. | 356/85 |
| 3,811,778 | 5/1974 | Hadeishi | 356/85 |

OTHER PUBLICATIONS

Mislan; Atomic Energy of Canada Limited; Rep. No. 1941; Apr. 1964; FIG. 1.

Primary Examiner—Vincent P. McGraw
Attorney, Agent, or Firm—Walter Becker

[57] ABSTRACT

A method of and device for investigating samples by a flame-free atom absorption process, according to which the sample is first in a relatively small chamber heated so as to be atomized into an atom cloud which is subsequently together with a protective gas tangentially conveyed into a considerably larger chamber through which a bundle of measuring rays is passed.

4 Claims, 3 Drawing Figures

METHOD OF AND DEVICE FOR INVESTIGATING SAMPLES BY A FLAME-FREE ATOM ABSORPTION PROCESS

In my co-pending application, Ser. No. 571,487 filed Apr. 25, 1975, there has been described a device for checking samples by flame-free atom absorption measurements. According to this device the sample is in a tubular test chamber closed by an optically translucent window, heated electrically to such high temperatures that the sample is atomized so as to form an atom cloud, and a measuring ray bundle is passed through said atom cloud. With these checks or tests, the sensitivity and the reproductivity of the measurement depends decisively on the speed at which the entire sample is atomized and how long in comparison thereto the atom cloud can be held in the path of the rays. Each freed atom is due to the gas flow and the thermo diffusion expelled very quickly out of the tube. The average staying time in the tube is shorter than the time period required for the complete atomization of the sample so that never all atoms are simultaneously in the path of the rays and consequently the maximum possible extinction will never be realized. If the successive generation of the atom cloud is additionally impeded by a foreign substance matrix, the reproductivity of the measurements is considerably reduced. With direct ascertainments, this will cause considerable difficulties in the sea water, in the biological material, and in the solutions which form during the extraction of heavy metals with complex formers.

It is therefore, an object of the present invention by certain features of the method to produce a possibly complete atom cloud not only in conformity with the suggestion set forth in applicant's above mentioned co-pending application Ser. No. 571,487, but also in such a way that the entire atom cloud is formed as spontaneously as possible and enters the path of the ray with the smallest possible initial dimensions.

This object and other objects and advantages of the invention will appear more clearly from the following specification in connection with the accompanying drawing, in which.

The method according to the present invention is characterized primarily in that the atom cloud is first formed in a separate chamber of smaller diameter and then is transferred into the test chamber which surrounds the bundle of measuring rays.

Figure 1:
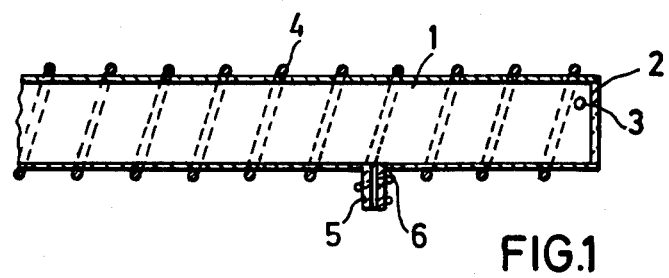
FIG. 1 represents a schematic axial section through a test chamber according to the present invention.

Referring now to the drawings in detail, the tubular measuring cell 1 illustrated in FIG. 1 is closed at one end thereof by means of a quartz window 2. In the vicinity of said quartz window 2 there is provided the entry 3 for the protective gas. For purposes of heating the measuring cell 1 there is provided a heating coil 4 which surrounds the tubular body of the cell 1.

In contrast to the heretofore known devices, the atom cloud is generated in a separate chamber prior to entering the actual test chamber. The atom cloud passes through a lateral opening 6 of the test chamber into the measuring cell 1.

Figure 2:
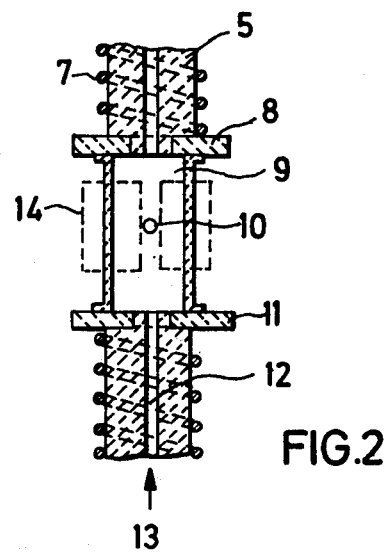
FIG. 2 represents an axial section through a test tube shown in the lower part of FIG. 1 but on a considerably larger scale than FIG. 1.

The specific design of the test tube 5 is illustrated in FIG. 2. The lateral extension of this test tube 5 may consist of quartz and may be heated indirectly. It is important that the test tube is so mounted that a gas flow passing therethrough enters the measuring cell 1 tangentially. The cross section of the opening 6 may with a wall thickness of a plurality of millimeters amount to about 1 mm. The indirect heating for the test chamber 5 may be effected by electrical coil 7. At the end of the test tube 5 there is a flange 8 preferably consisting of graphite, which takes care of the current supply to the adjacent atomizing cell 9. The atomizing cell 9 may consist of a thin-walled graphite pipe having a length of for instance 20 mm and an inner diameter of about 3 mm and an outer diameter of about 5 mm. The charging of the atomizing cell is effected through an inlet opening 10 adapted to be closed by a graphite cone.

The other end of the atomizing cell 9 is provided with a flange 11 and a heatable capillary pipe 12. Similar to the entrance to the atomizing cell 9 as indicated at 13, the protective gas can be conveyed through the capillary pipe 12 into the atomizing cell 9. Prior to the atomization, the temperature determination of the atomizing cell 9 may be effected if desired by a removable cooling body 14.

The atomizing cell need by flanged on only during the atomization of the test pipe if a high test frequency should so require. A current shock through the graphite pipe of the atomizing cell generates the atom cloud by heating, which atom cloud is then together with a small-dosed quantity of protective gas conveyed through bore 13 through the lateral extension to the test tube 5.

Figure 3:
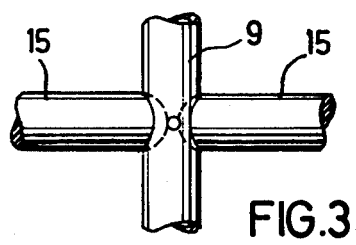
FIG. 3 is a diagrammatic illustration of a modified atomizing cell.

FIG. 3 shows an additional possible embodiment of the atomizing cell. In this instance, the supply of current is effected by two lateral graphite bars 15 as they are known with greater dimensions in connection with a carbon rod atomizer.

It is, of course, to be understood that the present invention is, by no means, limited to the specific showing in the drawing but also comprises any modifications within the scope of the appended claims.

What I claim is:

1. A device for investigating samples by means of the flameless atom absorption process having measuring rays passing through the samples, which includes in combinaton: a tubular measuring cell closed at one end by an end wall translucent to said rays, electric heating means surrounding said cell for heating the latter to high temperatures, inlet means substantially tangentially leading into said measuring cell, small auxiliary chamber means including additional heating means for atomizing only the sample to be investigated, said auxiliary chamber means communicating through said first inlet means with the interior or said measuring cell and having second inlet means for conveying the substance to be atomized entirely into said auxiliary chamber means, said auxiliary chamber means also having third inlet means for admitting protective gas into said chamber means and having means for heating said protective gas, and means for passing a bundle of measuring rays through said translucent end wall and the tubular measuring cell having the atom cloud of the sample being investigated therein.

2. A device in combination according to claim 1, in which said end wall is an optically translucent quartz window closing one end of said cell, and also includes fourth inlet means in the proximity of said window for admitting protective gas into said cell.

3. A device in combination according to claim 1, in which said third inlet means includes a capillary tube.

4. A method of investigating samples by a flame-free atom absorption process in a test chamber having tubular form closed at only one end by an optically translucent quartz window and electrically heatable to high temperatures causing atomization of an atom cloud, which includes in combination the steps of: atomizing the sample to be investigated to form an atom cloud in a first separate auxiliary chamber having small dimensions relative to said test chamber heating a protective gas and passing the thus formed atom cloud together with the heated protective gas tangentially entirely into the larger test chamber through an inlet spaced from said quartz window, and finally passing a bundle of measuring rays through said atom cloud, said bundle of measuring rays passing through said atom cloud being surrounded by the test chamber.

* * * * *